(12) United States Patent
Lund-Johansen

(10) Patent No.: US 7,897,407 B2
(45) Date of Patent: Mar. 1, 2011

(54) MULTICOLORED PARTICLES

(75) Inventor: Fridtjof Lund-Johansen, Jar (NO)

(73) Assignee: Rikshospitalet HF, Oslo (NO)

( * ) Notice: Subject to any disclaimer, the term of this patent is extended or adjusted under 35 U.S.C. 154(b) by 46 days.

(21) Appl. No.: 11/995,418

(22) PCT Filed: Jul. 10, 2006

(86) PCT No.: PCT/NO2006/000269
§ 371 (c)(1),
(2), (4) Date: Jul. 22, 2008

(87) PCT Pub. No.: WO2007/008084
PCT Pub. Date: Jan. 18, 2007

(65) Prior Publication Data
US 2009/0137060 A1 May 28, 2009

(30) Foreign Application Priority Data
Jul. 11, 2005 (NO) .................................. 20053373

(51) Int. Cl.
*G01N 21/77* (2006.01)
*C12Q 1/00* (2006.01)
(52) U.S. Cl. .............. 436/172; 436/164; 208/12; 525/50
(58) Field of Classification Search .............. 436/172, 436/164; 208/12; 525/50
See application file for complete search history.

(56) References Cited

U.S. PATENT DOCUMENTS

| 4,717,655 | A | 1/1988 | Fulwyler |
| 4,774,189 | A | 9/1988 | Schwartz |
| 5,073,498 | A | 12/1991 | Schwartz et al. |
| 5,194,300 | A | 3/1993 | Cheung |
| 5,206,143 | A * | 4/1993 | Horan et al. .................. 435/7.24 |
| 5,326,692 | A | 7/1994 | Brinkley et al. |
| 5,573,909 | A | 11/1996 | Singer et al. |
| 5,716,855 | A | 2/1998 | Lerner et al. |
| 5,723,218 | A | 3/1998 | Haugland et al. |
| 5,786,219 | A | 7/1998 | Zhang et al. |
| 6,599,331 | B2 | 7/2003 | Chandler et al. |

(Continued)

FOREIGN PATENT DOCUMENTS

WO 9937814 A 7/1999

(Continued)

OTHER PUBLICATIONS

Wolfgang J. Parak, Biological Applications Of Colloidal Nanocrystals, Nanotechnology 14 (2003) R15-R27, Institute Of Physics Publishing Ltd., U.K.

*Primary Examiner* — Krishnan S Menon
*Assistant Examiner* — Allison Gionta
(74) *Attorney, Agent, or Firm* — Volpe and Koenig, P.C.

(57) ABSTRACT

A set of polymer particles stained with at least two fluorescent dyes is presented. At least 16 subsets of particles can be resolved on the basis of variable emission from the at least two fluorescent dyes where emission from at least one dye derives from a fluorescent dye covalently attached to the particle surface. All particles in the set of polymer particles can bind a uniform amount of a capture reagent. A method for the preparation of the set of polymer particles as well as a kit including the set of polymer particles is also presented as well as methods and uses of the set of polymer particles.

20 Claims, 11 Drawing Sheets

U.S. PATENT DOCUMENTS

| | | |
|---|---|---|
| 6,649,414 B1 | 11/2003 | Chandler et al. |
| 6,838,289 B2 * | 1/2005 | Bell et al. ............. 436/172 |
| 7,442,553 B2 * | 10/2008 | Kobayashi et al. ......... 436/85 |
| 2003/0028981 A1 | 2/2003 | Chandler et al. |
| 2003/0143159 A1 * | 7/2003 | Achilefu et al. ........... 424/9.6 |
| 2004/0101822 A1 | 5/2004 | Wiesner et al. |

FOREIGN PATENT DOCUMENTS

| | | |
|---|---|---|
| WO | 0016101 A | 3/2000 |
| WO | 0039335 A | 7/2000 |
| WO | 0113120 A | 2/2001 |
| WO | 03042695 A | 5/2003 |
| WO | WO 2005026225 | 3/2005 |

\* cited by examiner

MULTICOLORED PARTICLES

FIELD OF INVENTION

The present invention relates to a set of polymer particles stained with at least two fluorescent dyes, wherein at least 16 subsets of particles can be resolved on the basis of variable emission from the at least two fluorescent dyes wherein emission from at least one dye derives from a fluorescent dye covalently attached to the particle surface, and wherein all particles in said set of polymer particles can bind a uniform amount of a capture reagent. The invention also relates to a method for the preparation of said set of polymer particles as well as a kit comprising said set of polymer particles. The invention further relates to methods and uses of said set of polymer particles.

BACKGROUND

It is recognized that two or more dyes of varying proportions could be used to increase the permutation number of unique combinations of dyes in a single particle. The unique emission wavelengths and fluorescence intensities could be useful for multiparameter or multiplex analysis of a plurality of analytes in the same sample.

Three methods of making colored, fluorescent beads have been disclosed, including: (a) covalent attachment of dyes onto the surface of the particle (e.g. U.S. Pat. No. 4,774,189 Schwartz; U.S. Pat. No. 5,194,300 Cheung), (b) internal incorporation of dyes during particle polymerization (e.g. U.S. Pat. No. 5,073,498 Schwartz; U.S. Pat. No. 4,717,655 Fulwyler), and (c) dyeing after the particle has been already polymerized (e.g. L. B. Bangs, Uniform Latex J Particles; Seragen Diagnostics Inc. 1984).

U.S. Pat. No. 5,194,300 Cheung and U.S. Pat. No. 4,774,189 Schwartz disclose fluorescent microspheres that are coated by covalently attaching either one or a plurality of fluorescent dyes to their surface. However, the features of the particles do not meet the specifications required for multiplex analysis: In U.S. Pat. No. 4,774,189 Schwartz fluorescent proteins are coupled to particles to generate standards for flow cytometric analysis using similar fluorescent proteins. It discloses that particles with different intensities of fluorescence can be generated by covalently attaching fluorescent proteins to particles. However, since these particles were designed for standardization purposes, no attempts were made to couple two fluorochromes simultaneously to the particles. Furthermore, no attempts were made to attach a capture reagent molecule to the same particles. The fluorescent probes used are proteins that denature in harsh conditions such as those used for hybridization of DNA in buffers used for immunoprecipitation that contain denaturing detergents such as SDS. Furthermore, attachment of fluorescent proteins to particles will compromise the binding of capture reagents such as antibodies to the same particles. Their method is therefore not applicable for generating multicolored particles for multiplex analysis. U.S. Pat. No. 5,194,300 Cheung reports small (300 angstrom) fluorescent particle that could be used to enhance signals for detection. The inventors show that it was possible to generate particles that have a single fluorescence intensity and a capture reagent bound to their surface. It was not reported whether binding of the dyes interfere with subsequent binding of biomolecules. Moreover, no attempts are made to generate particles with several different intensities of fluorescence or to couple two colors to the same particle.

The second approach to particle dying is represented by U.S. Pat. No. 5,073,498 Schwartz and U.S. Pat. No. 4,717,655 Fulwyler. The former discloses two or more fluorescent dyes added during polymerization process and randomly dispersed within the body of the particle. However, when such particles are exposed to a single excitation wavelength only one fluorescent signal is observed at a time and thus these particles are not useful for multiparameter analysis especially in a flow cytometry apparatus with a single excitation light source. U.S. Pat. No. 4,717,655 Fulwyler discloses two dyes mixed at five different ratios and copolymerized into a particle. Although five populations of beads were claimed as being obtainable, the fluorescent properties of these beads are not provided. In conclusion, both U.S. Pat. No. 5,073,498 Schwartz and U.S. Pat. No. 4,717,655 Fulwyler represent complex and costly methods for producing multicolored particles comprising internal incorporation of dyes.

The principle of the third method, i.e., internally embedding or diffusing a dye after a particle has been already polymerized was originally described by L. B. Bangs (Uniform Latex J Particles; Seragen Diagnostics Inc. 1984, p. 40) and consists of adding an oil-soluble or hydrophobic dye to stirred microparticles and post-incubation washing off the dye. The microspheres used in this method are hydrophobic by nature. This allows adopting the phenomenon of swelling of such particles in a hydrophobic solvent, which may also contain hydrophobic fluorescent dyes. Once swollen, such particles will absorb dyes present in the solvent mixture in a manner reminiscent to water absorption by a sponge. The level and extent of swelling is controlled by incubation time, the quantity of cross-linking agent preventing particle from disintegration, and the nature and amount of solvent(s). By varying these parameters one may diffuse a dye throughout particle or obtain fluorescent dye-containing layers or spherical zones of desired size and shape. Removing the solvent terminates the staining process. Microparticles stained in this manner will not "bleed" the dye in aqueous solutions or in the presence of water-based solvents or surfactants such as anionic, nonionic, cationic, amphoteric, and zwitterionic surfactants. U.S. Pat. No. 5,723,218 Haugland discloses diffusely dyeing microparticles with one or more dipyrrometheneboron difluoride dyes by using a process, which is essentially similar to the Bangs method. However, when beads internally stained with two separate dipyrrometheneboron dyes, were excited at 490 nm wavelength, they exhibited overlapping emission spectra. Hence, the beads were monochromatic and not multicolored. U.S. Pat. No. 5,326,692 Brinkley et al; U.S. Pat. No. 5,716,855 Lerner et al; and U.S. Pat. No. 5,573,909 Singer et al. disclose fluorescent staining of microparticles with two or more fluorescent dyes. However, dyes used in these processes have overlapping excitation and emission spectra allowing energy transfer from the first excited dye to the next dye and through a series of dyes resulting in emission of light from the last dye in the series. This process was intended to create an extended Stokes shift, i.e., a larger gap between the excitation and emission wavelength, and not the emission of fluorescence from each dye simultaneously. Thus, due to various reasons such as dye-dye interaction, overlapping spectra, non-Gaussian emission profiles and energy transfer between neighboring dyes, the demand for multicolored beads simultaneously emitting fluorescence at distinct peaks was not satisfied.

U.S. Pat. No. 5,786,219 Zhang devised microspheres with two-color fluorescent "rings" or microspheres containing a fluorescent spherical "disk" combined with a fluorescent ring. Nevertheless, such beads, designed for calibration purposes, cannot be used in multiparameter analysis since two dyes were mixed only at one fixed ratio. However, the highest number of dyes ratios ever attempted with at least two dyes never exceeded five.

Chandler et al (U.S. Pat. No. 6,599,331) disclose a method that is essentially similar to that disclosed by Bangs and later applied by Haugland, Brinkley and Lerner. The main difference being the choice of fluorescent dyes. The inventors were able to find a combination of dyes that resulted in dual emission from the particles. However, this method may be limited to a few selected dyes since previous results by Haugland Brinkley and Lerner showed that energy transfer resulted in monochromatic emmission. In U.S. Pat. No. 6,649,414, Chandler et al disclose a method where nano-particles are dyed according to the same procedure as that disclosed in U.S. Pat. No. 6,599,331. These nanoparticles were then attached to the surface of larger polymer particles to generate a new particle consisting of a core particle and a layer of variable numbers of nano-particles on the surface. Such particles will, however, have an irregular surface and therefore highly variable light scattering properties and most likely a high tendency for aggregation in solution. In addition, non-specific binding of proteins from e.g. a cell lysate will tend to increase when the surface is irregular.

The following challenging aspects are relevant when developing a multi-colored particle:

1. Since surface labeling occurs via reactive groups on the particle, binding of fluorescent dyes and capture reagents will compete for the reactive groups on the particle. Thus, particles that are first labeled with different amounts of dyes would not be expected to bind similar levels of reagent used to bind the analyte. Alternatively, particles that have first bound the reagent used to bind the analyte would be expected to have few groups available for the reactive groups of the fluorescent dyes.

2. Surface labeling with multiple fluorescent compounds might be expected to lead to a large degree of fluorescence energy transfer between the dyes. This would greatly limit the number of codes that can be generated. Color-coding based on two or more fluorescent probes implies that the emission and, or absorption spectra of the probes are sufficiently different to allow simultaneous independent detection of the two probes. When two probes are in close proximity fluorescence energy transfer may occur. This implies that the light emitted by one of the probes is absorbed by the second and thus quenched. This phenomenon is well known and may occur even between probes that have large differences in emission and absorption spectra. An example is Phycoerythrin and Cy.5, where the emission spectrum of Phycoerythrin and the absorption spectrum of Cy5 is separated by >100 nm. In this case the fluorescence of Phycoerythrin is completely quenched by Cy5. When dyes are incorporated into the polymer, they are distributed throughout the volume of the particles. The surface area of the particle is a much smaller distribution area for the probes. Therefore one might expect that the probes would be in close proximity. This could limit the number of measurable color codes to the extent that true multiplex color coding would be impossible.

3. It is expected that fluorescent dyes bound to the surface of particles may interfere with fluorescent signals from the analyte due to fluorescence energy transfer. Thus, if the fluorescent probe used to detect the analyte can transfer energy to the dye used for color-coding or vice versa, one would expect that the analyte signal would be different on particles with different color codes.

4. Furthermore, one would expect that surface labeling is not sufficiently stable to allow discrimination of small differences in fluorescence when particles are subjected to storage or reactions that require harsh conditions such as high temperatures.

5. Lastly, fluorescent dyes may undergo changes in spectral characteristics upon binding to monodisperse latex spheres.

In our opinion, no reliable microsphere populations or subsets emitting, upon exposure to a single excitation wavelength, multiple fluorescent signals of variable intensity and at spaced, optically distant wavelengths from surface-bound dyes or a combination of internal and surface-bound dyes have so far still been disclosed. In particular, there is a great need for particles with said characteristics which further permit use of a wide range of commercially available reactive forms of fluorescent dyes, which are produced by a simple and cost-effective method and which can be dyed after labeling with uniform levels of a capture reagent.

SUMMARY

The instant invention describes a novel set of polymer particles stained with at least two fluorescent dyes, wherein at least 16 subsets of particles can be resolved on the basis of variable emission from the at least two fluorescent dyes wherein emission from at least one dye derives from a fluorescent dye covalently attached to the particle surface, and wherein all particles in said set of polymer particles can bind a uniform amount of a capture reagent. Surprisingly, the present invention shows that it is possible to generate at least 100 different color-codes on particles first and then obtaining highly uniform levels of a capture reagent. Moreover, the disclosed data show that 100 different color codes (subsets of particles) can be generated using particles that have first been reacted with a single concentration of a capture reagent. The present invention demonstrates that (1) even though fluorescence energy transfer does occur, it is still possible to generate 100 different color codes (subsets of particles) via surface labeling; (2) that fluorescence energy transfer between the probe used for detection and that used for color-coding does not occur. Thus particles that were color-coded by surface labeling with different amounts of the fluorescent dyes Alexa 647 and Alexa 488 had the same intensity of phycoerythrin fluorescence when incubated with the same amount of a phycoerythrin-labeled analyte. This is an unexpected finding since Alexa 647 is known as a very effective acceptor for phycoerythrin. (3) Present data show that fluorescent properties of the color-coded particles is unchanged by boiling of the particles; (4) that dyes, like Alexa 647, undergoes drastic time-dependent changes in their spectral properties upon binding to monodisperse latex spheres. Quite unexpectedly, this far-red dye has considerable green fluorescence following storage of particles at 4 C. (5) Finally, the present invention demonstrates that changes in spectral characteristics can be avoided by the use of maleimide derivatives of dyes and by storing dyed particles at 20 C in a cryopreservation medium consisting of PBS with 50% trehalose.

Hence, the inventors believe the current invention accommodate the above-mentioned needs by providing a surface-multicolored set of particles, as well as methods and uses thereof, allowing a plurality of defined subsets of stained colored microparticles distinguishable by a subtle variation in fluorescence signal resulting from the combination of various dyes of distinct color and having variable intensity of color emission. The present surface labeling permits the use of a wide range of reactive forms of fluorescent dyes that are commercially available. The labeling process is greatly simplified compared to incorporation of dyes into the polymer. In addition, it is possible to dye particles that are already labeled with uniform levels of a capture reagent.

DETAILED DESCRIPTION OF THE PREFERRED EMBODIMENTS

Figure 1:
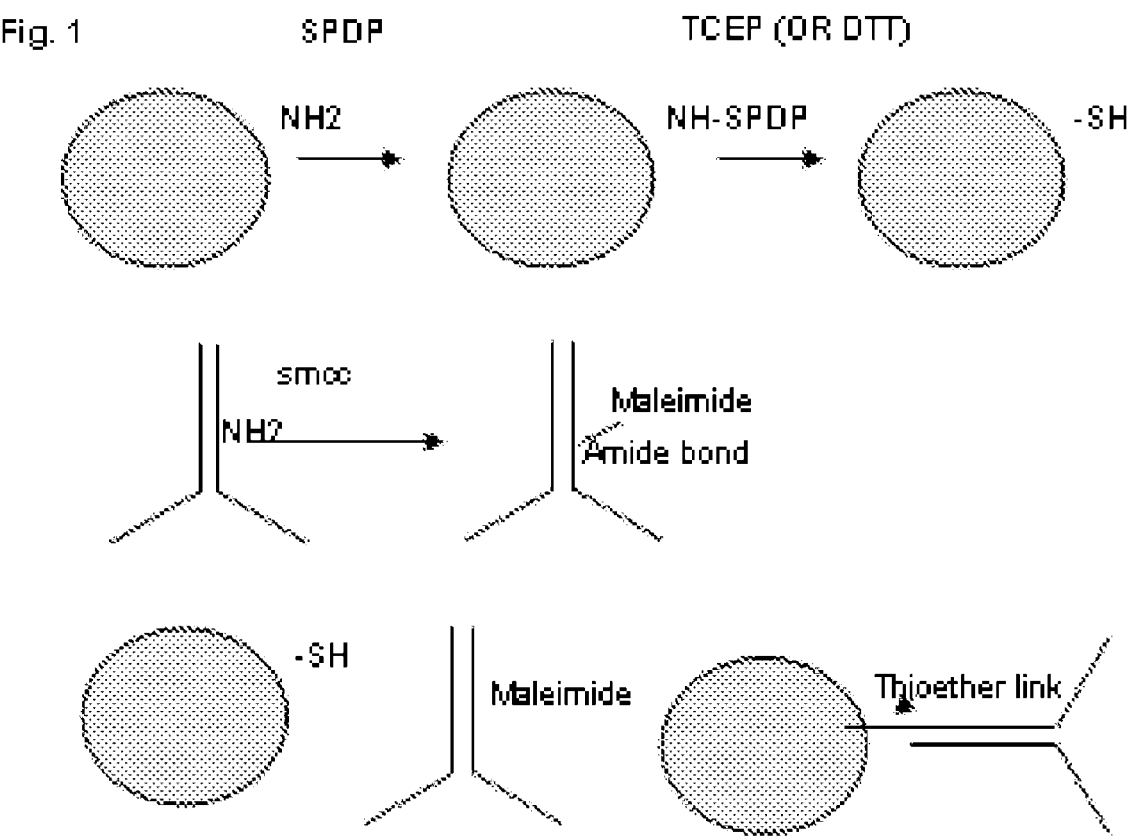
FIG. 1 Attachment of crosslinker to beads, priming antibodies, and attaching the antibody to the particle via a crosslinker.

The current invention comprises a set of polymer particles stained with at least two fluorescent dyes, wherein at least 16 subsets of particles can be resolved on the basis of variable emission from the at least two fluorescent dyes wherein emission from at least one dye derives from a fluorescent dye covalently attached to the particle surface, and wherein all particles in said set of polymer particles can bind a uniform amount of a capture reagent.

Said subset of polymer particles is herein defined as a group of polymer particles having a unique color code that can be resolved on the basis of their variable emission from the at least two fluorescent dyes. Variable emission is herein defined to also include no emission.

Said at least 16 subsets of particles preferably being at least 25 or 36 subsets of particles, and even more preferably being at least 48 subsets of particles.

The number of subsets of particles that may be resolved on the basis of variable emission from said at least two fluorescent dyes can be directly and positively verified without undue experimentation by e.g. using the method described in example 2.

Uniform amount and/or uniformly labeled is herein defined as an amount or a labeling that does not significantly vary between particles within the set, but is even and regular throughout.

The present invention also relates to a said set of polymer particles, wherein said dyes are attached in defined concentrations. Defined concentrations is herein defined as the amount of each dye that is attached to the particles in a specific subset of particles. The amount of each dye is herein defined to also include no dye.

The present invention also relates to said set of polymer particles, wherein said at least one fluorescent dye that is covalently attached to the particle surface is covalently attached via a bifunctional crosslinker, biotin-streptavidin chemistry or directly to each particle.

The present invention also relates to said set of polymer particles, wherein all particles in said set of polymer particles contain sufficient binding sites for uniform covalent attachment of capture reagent. Said binding sites preferably being free SH- or amino-groups.

The present invention also relates to said set of polymer particles, wherein all particles in said set of polymer particles may be uniformly labeled with a capture reagent, wherein the capture reagent optionally has attached fluorescent dyes. Said capture reagent may be non-covalently attached to the particles. Preferably, said capture reagent may be covalently attached via a bifunctional crosslinker, biotin-streptavidin chemistry or directly to each particle. Said capture reagent may be any molecule capable of interacting with a molecule of interest, e.g. a protein in a biological assay. Said capture reagent may be a protein, e.g. antibody-based molecule or a nucleic acid e.g. DNA or RNA.

The bifunctional crosslinker may be any suitable crosslinker, preferably the crosslinkers according to Table 1, more preferably, a crosslinker based on maleimide-thiol chemistry. The crosslinker may be homo- or heterobifunctional, however, heterobifunctional crosslinkers are preferred. In an embodiment of the current invention the crosslinker is SPDP.

Suitable fluorescent dyes or fluorochromes, hereafter named dyes, are known within the art and examples are listed in Table 2. In a preferred embodiment of the current invention the dyes may be UV/violet excitable, 488 nm excitable, 532 nm (YAG) excitable, 595 nm (Krypton) excitable, 633 nm excitable, Infrared excitable, 488 nm excitable, 633 nm excitable Tandem conjugates of PE and APC, Tandem conjugates of reactive dyes (e.g. Alexa dyes) 488 nm excitable and/or quantum dots. Even more preferably the fluorescent dyes may be hydrophilic forms of cyanine dyes such as reactive forms of Alexa 488 and 647.

Polymer particles suitable as a starting material for the current invention is known in the art and can be obtained from commercial manufacturers. The initial particles may be formed of e.g. polyvinyl chloride, polyvinyl toluene, styrene, or methymethacrylate with polyvinyl toluene and the particles are preferably less than 100 μm in diameter.

Other examples of microspheres are brominated polystyrene, polyacrylic acid, polyacrylonitrile, polyacrylamide, polyacrolein, polybutadiene, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, or combinations thereof.

The present invention also relates to said set of polymer particles, wherein the particles may be monodispersed particles. Monodisperse particle is herein defined as a particle with only one molecular mass.

The set of particles of the invention further comprise several fluorescent dyes or fluorochromes, preferably at least two fluorescent dyes or fluorochromes, and most preferred two fluorescent dyes or fluorochromes.

Dyed nanoparticles are not regarded as fluorochromes in the present disclosure.

The surface of the particles, not the core, should be dyed in defined concentrations.

A certain absorption of dye radially within the particle's surface may occur. The above particles render possible heterogenous set of polymer particles with particle subsets emitting unique combination of fluorescent light and carrying a particular capture reagent, e.g. an antibody.

Another aspect of the current invention is a method for the preparation of the set of polymer particles according to the invention comprising, in either sequence:

Attaching at least two fluorescent dyes in defined concentrations to the set of polymer particles according to the invention, wherein at least one dye is covalently attached to the particle surface, and optionally attaching different capture reagents of interest to different subsets of polymer particles, wherein said capture reagent may be covalently attached directly to each particle or via a bifunctional crosslinker or biotin-streptavidin chemistry and optionally has attached fluorescent dyes.

Preferably, the method is executed as described in the disclosed examples of this application.

Another aspect of the current invention is a set of polymer particles prepared according to the above method.

The set of polymer particles of the invention may be used for specific binding of biomolecules, including native and modified forms of polypeptides and polynucleotides, and allows parallel analysis of a multitude of analytes. For example, the phosphorylation status of a multitude of proteins can be assessed in parallel by means of the particles of the invention and a flow cytometer. Accordingly, a further aspect of the current invention is the use of the set of particles according to the invention in multiplex analysis and/or in the field of diagnostics.

A further aspect of the present invention is the set of polymer particles according to the invention for use in multiplex analysis and/or for diagnostic use.

A further aspect of the present invention relates to a diagnostic method or a multiplex analysis method comprising the following steps:

(a) attaching different capture reagents of interest to different subsets of polymer particles, wherein each subset of polymer particles then having a specific capture reagent attached.

(b) mixing said set of polymer particles with a sample of interest (c) analyzing said set of particles by flow cytometry.

A further aspect of the invention is a kit comprising the set of particles according to the invention.

EXAMPLES

1. General Considerations 1.1 Attachment of a Capture Reagent to the Particles This is performed by incubation of particles with the same concentration of a capture reagent. Covalent binding is best achieved by first incubating particles with a crosslinker (Table I). The preferred method is to use maleimide-thiol chemistry. The heterobifunctional crosslinker SPDP is attached to amino-derivatized particles and the pyridyldisulfide group is reduced with TCEP or DTT. A maleimide group is attached to the capture reagent (e.g. an antibody or protein A or protein G) by incubation with another heterobifunctional crosslinker such as SMCC (Table I). The modified reagent is then incubated with the particles at pH5.

Alternatively, maleimide groups can be added to the particles with the crosslinker SMCC. In this case the protein (modified with SPDP or not) is reduced with TCEP at pH5.0 to generate free —SH groups. The results are similar. Other types of homo- and hetero-bifunctional crosslinking agents have been described and would be expected to provide similar results. (Table I)

Finally, proteins such as antibodies may be bound to particles by physical adsorption. This does not provide covalent coupling. However, for several applications, the binding obtained by physical adsorption is sufficiently stable. This is a routinely used way to couple proteins to latex in assays such as ELISA.

1.2. Color-Coding

Color coding is performed by incubation of particles with defined concentrations of reactive forms of two or more fluorescent dyes. Bound dye is separated from unbound dye by centrifugation of particles, removal of supernatant and the particles are suspended in a new buffer. Color coding can be performed after binding of a general capture reagent such as anti-mouse IgG. Alternatively, particles can be dyed first and then coupled to a capture reagent at a later time point. In most cases higher concentrations of dyes are necessary when color coding is performed after the binding of a capture reagent.

Example 2

Figure 2:
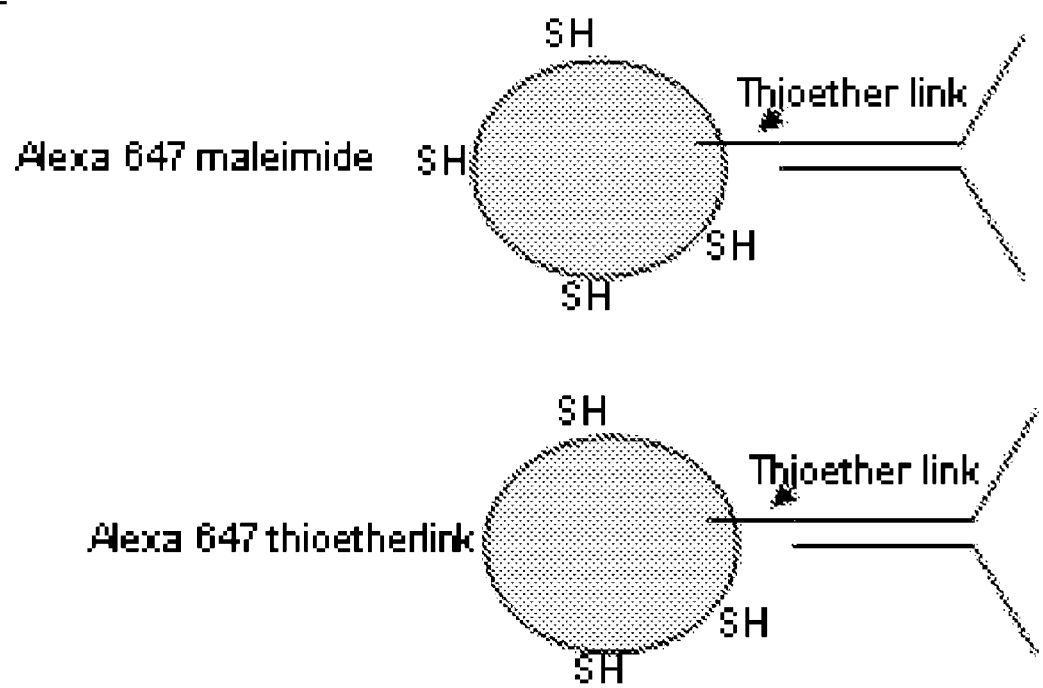
FIG. 2 Particles
Figure 6:
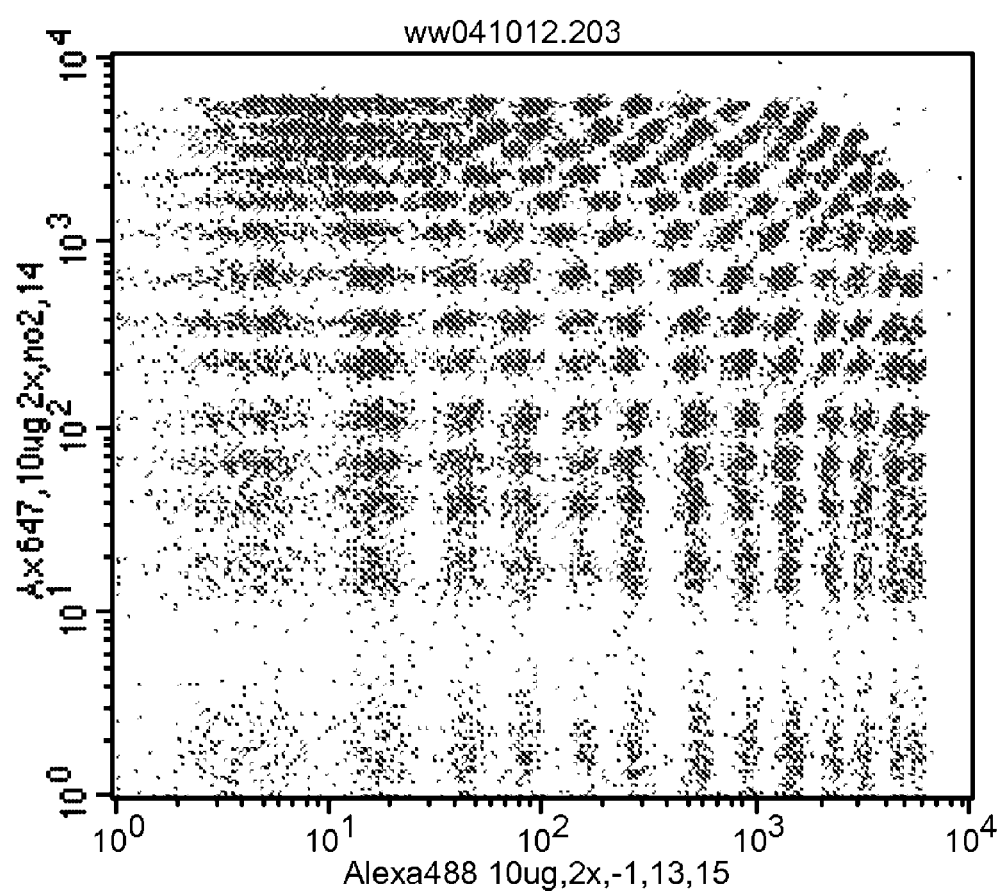
Figure 7:
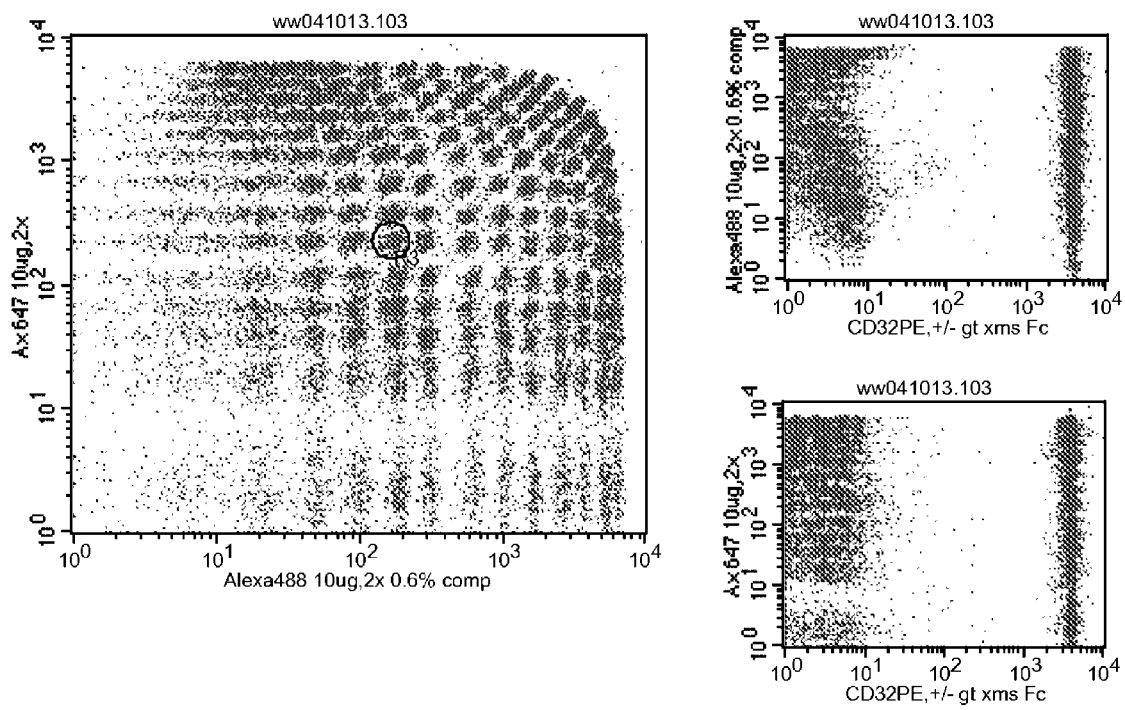
FIG. 7 A mixture of particles dyed with Alexa 488 and Alexa 647 were split in two, one was incubated with SMCC modified Goat anti-mouse IgG Fc, the other not. The two were then mixed again, blocked with PBS containing 10% FCS and 1% Tween 20 and then incubated with a PE-labeled mouse IgG antibody. The results show uniform staining of particles with antibody regardless of their fluorescence properties.
Figure 8:
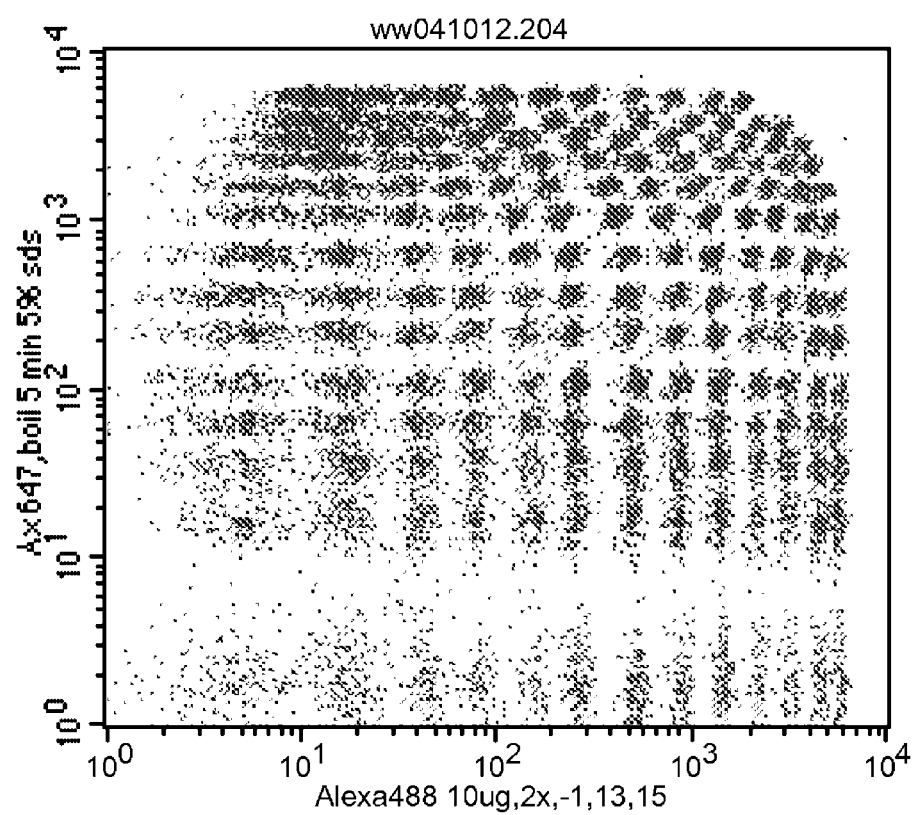
FIG. 8 Mixed particles were boiled for 5 min with 10% SDS to test stability of the fluorescent signals.
Figure 9:
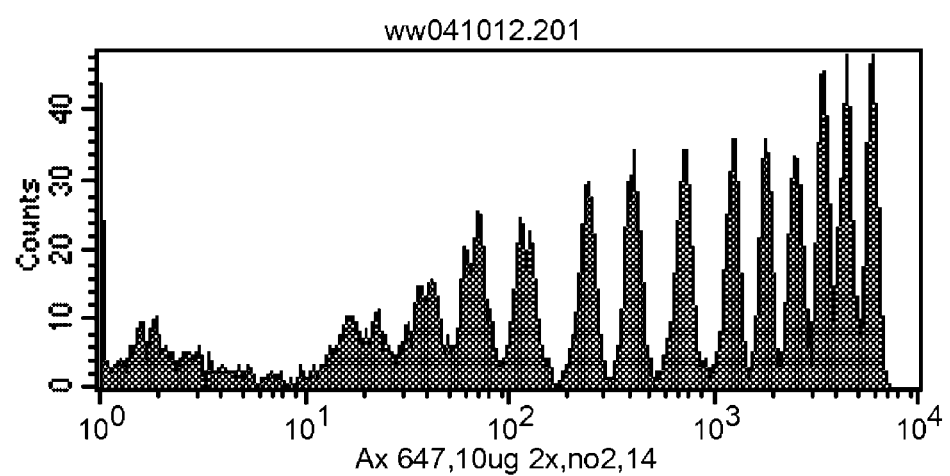
FIG. 9 Amino-terminated microspheres were incubated with SPDP, reduced with TCEP and then incubated with two-fold dilutions of Alexa 647 maleimide. Particles were then washed five times. Fluorescence intensity of particles was measured with a FACSCalibur flow cytometer.

The preferred method is the use of maleimide-derivatives of dyes. These dyes bind to free —SH groups that remain following attachment of the capture reagent (FIG. 2). Preferred combinations are dyes with large differences in emission spectra such as Alexa 647 and Alexa 488. Dyes are dissolved at 1:1, 75 fold dilutions in MES buffer pH6.0 usually starting at 100-1000 ng/ml of dye. Particles with free —SH groups (see procedure for attaching capture reagents) are resuspended in MES buffer pH6. This procedure was followed and the batch was first split in 12 equal aliquots. Each was incubated with a different concentration of one maleimide dye at 37° C. with frequent mixing for 15 min and then, cooled to 4° C. and washed. Each aliquot was then split in 8 new aliquots. Each of the new aliquots was incubated with different concentrations of the second fluorescent dye. FIG. 6 shows that 96 different color codes were made by this procedure. FIG. 7 shows that all particles bind similar amounts of a capture reagent.

Example 3

Figure 3:
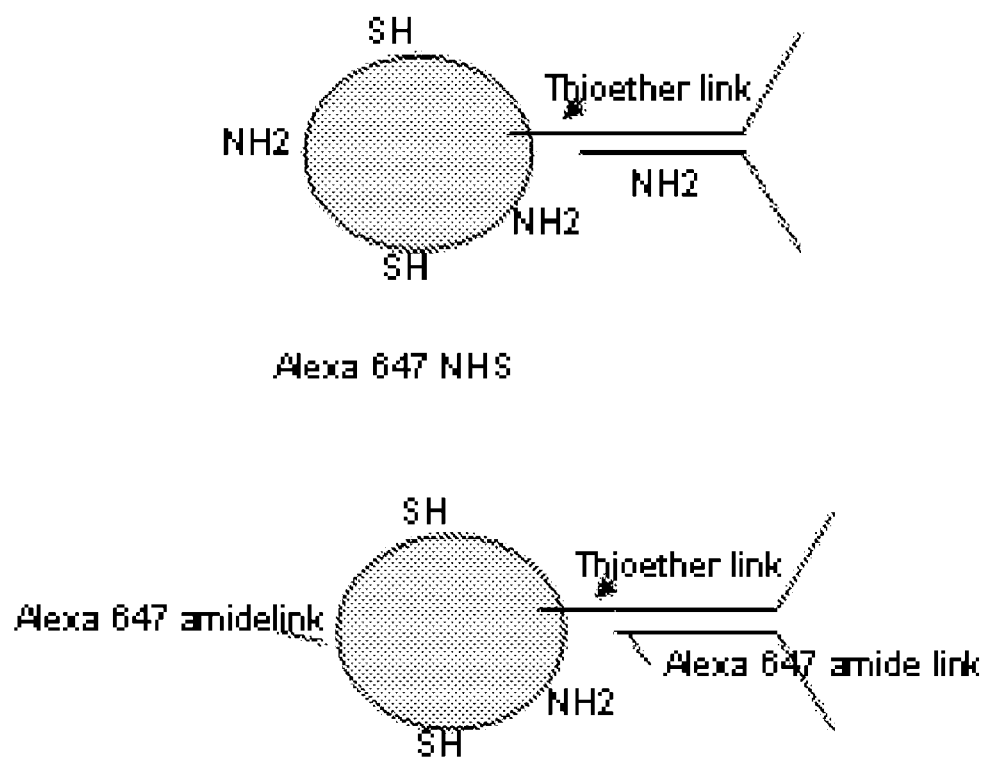
FIG. 3 Particles

The method can be extended to other reactive forms of fluorescent dyes. Amine-reactive forms such as N-hydroxysuccimidyl esters (NHS esters) bind to free amines on the capture reagent or amines that were not used for attachment of the crosslinker (FIG. 3). The reaction is performed at pH7.4 or higher.

Example 4

Figure 4:
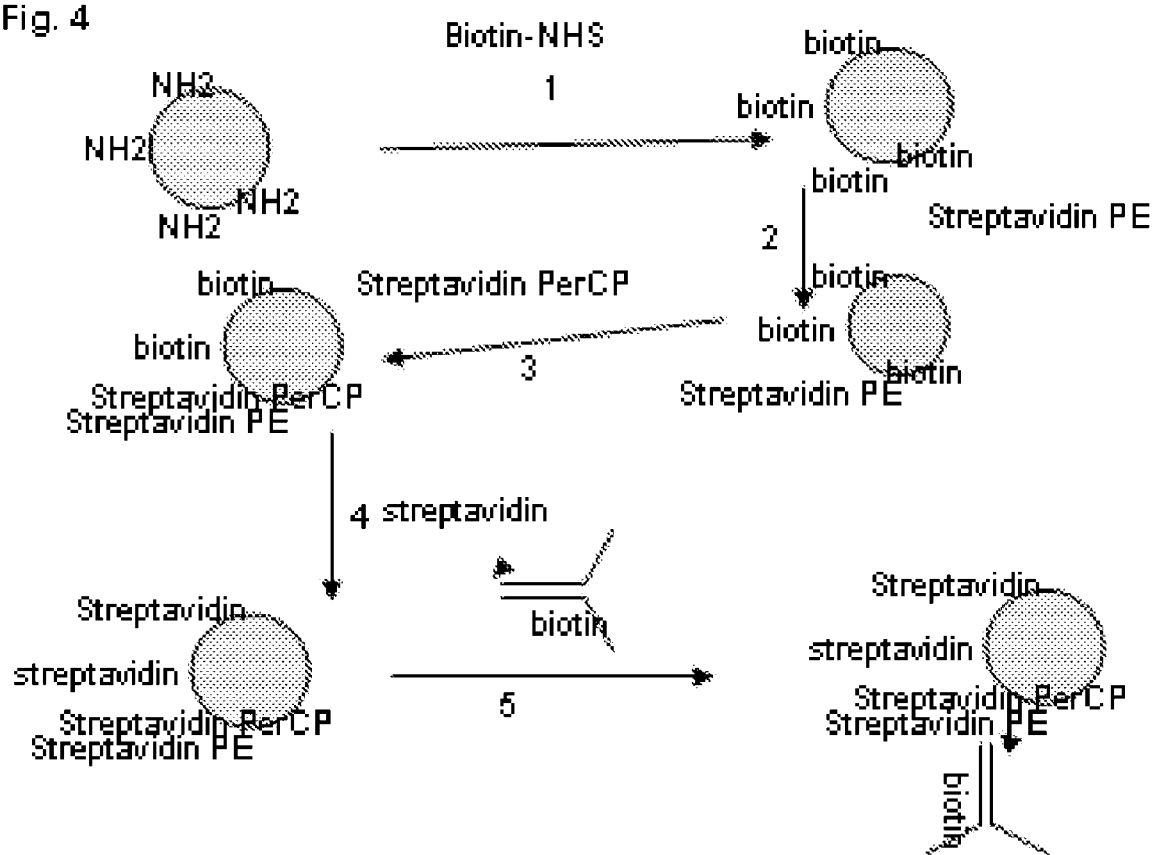
FIG. 4 Method of producing particles of the invention by employing biotin instead of a crosslinker FIG. 5 Multiplex analyis by flow cytometry FIG. 6 Particles stained with Alexa 647 maleimide were mixed as described, split in 16 equal aliquots and labeled with Alexa 488 maleimide.
Figure 5:
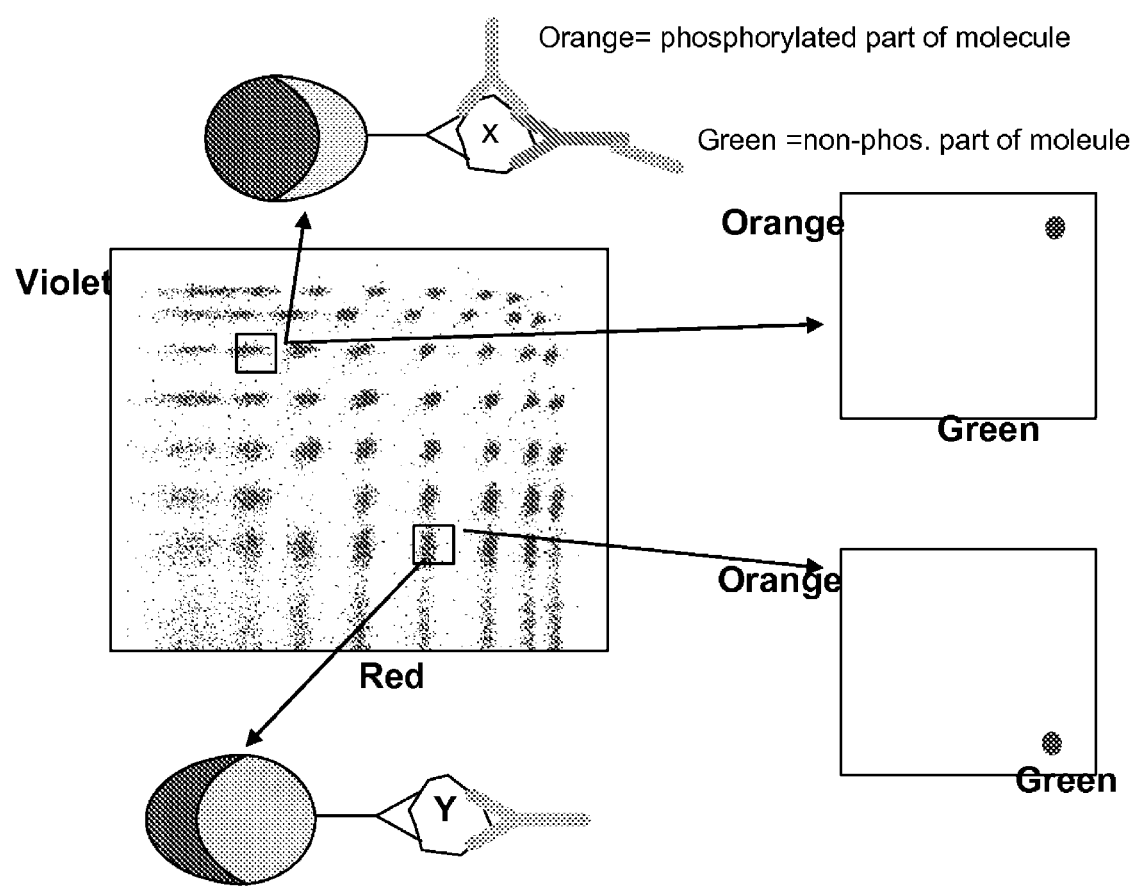

The method can be extended to using biotin instead of a crosslinker on the particle (FIG. 4). The particles are first incubated with reactive forms of biotin, then with variable concentrations of a streptavidin-fluorophore-conjugate such as streptavidin-Phycoerythrin, then with variable concentrations of a second streptavidin-fluorophore-conjugate such as Streptavidin PerCP. Finally, the particles are reacted with saturating concentrations of unlabeled streptavidin. The particles are finally reacted with a biotinylated capture reagent.

Example 5

Detailed Description of the Method to Generate a Multiplex with Anti-Mouse Igg as a General Capture Reagent a. Method for Coupling Antibodies and Dyes to Aminobeads.

Protein Coupling:

Materials:

Aminobeads, 7.74 um or 3.69 um from Bangs Laboratories. Stock: 10% solids stored at 4 C. Beads have free aminogroups on surface.

Crosslinkers: SPDP: one NHS arm that reacts with aminobeads, one disulphide arm that can be reduced and thus provides free-SH groups on beads.

Sulfo-SMCC: one NHS arm that binds to aminogroups on antibodies, one maleimide arm that binds to thiols on beads. Both crosslinkers are stored at −70 in DMSO the concentration of the stock is 10 mg/ml.

TCEP: a strong reducing agent, prepare a 100 mM solution in water before each experiment. (powder stored at room temp together with dry chemicals in our lab). Typically weigh out 3 mg in an eppendorf tube and add 100 ul water, mix well.

Buffers: PBS with 1% tween and 5 mM EDTA, MES 100 mM pH5.2, 100 mM MES pH6 with 1% tween and 5 mM EDTA.

Tubes: 15 ml polypropylene tubes, 1.5 ml Eppendorf tubes.

Gels for buffer exchange of proteins: Sepharose G50 fine, add 3.5 g powder to a 50 ml tube, fill with each buffer. Mix well and let it settle before use to avoid bubbles.

Columns for buffer exchange of proteins:

Microspin columns: can take 1 ml of gel, use for samples less than 100 ul Biospin columns: can take 2 ml of gel, use for samples up to 200 ul PD-10 columns: can take 10 ml of gel and are used up to 1.5 ml sample.

Use of Columns:

Microspin: add gel, place column on an eppendorf tube, cut off lid, spin first for 10 sec in the microfuge, discard fluid from Eppendorf tube. Place column on the eppendorf tube again and centrifuge for 30 sec. The column is now ready for use. Biospin: add gel, place column on a flow cytometry tube, centrifuge for 5 min at 1600 rpm. Vacuum away fluid from tube. The column is now ready for use.

PD-10: Add gel, place column on an eppendorf tube inside a 50 ml tube, centrifuge for 5 min at 1600 rpm. Discard the tubes, and place the column in new Eppendorf/50 ml tube. It is now ready for use.

Add sample to the center of the gel. Add 10% extra volume on top with wanted buffer. Spin 5 min 1600 rpm for Biospin and PD10, 30 sec in microfuge for microspin. The protein is in the tube at the bottom in the new buffer.

b. Procedure for Making an Array from 1 ml of Aminobeads.

Part 1. Coupling of Proteins to Beads.

1. Take out 0.5 mg protein, if it is in PBS, use as is, if not: buffer exchange on G-50 PBS, add 10 ul of SMCC stock per 1 ml of protein solution. Mix well and leave on the bench for 30 min-1 h (basically to all other steps of part 1 are done)

2. Add 1.5 ml Aminobeads to a 15 ml tube filled with 13 ml with PBS-Tween EDTA, centrifuge for 3 min at 1200 rpm.

2. Discard supernatant, whirlmix the pellet well and add 0.5 ml of PBS tween. Resuspend with a 1 ml pipette. Adjust volume to 10 ml and add 100 ul SPDP stock, mix well and rotate for 30 min at room temp.

3. Wash twice with PBS tween, adjust volume to 2 ml

4. Add 20 ul 100 mM TCEP, mix well and incubate 15 min at 37 C water bath, whirlmix every 5 min Wash with MES pH 5.2

Resuspend beads by adding 0.5 ml MES pH5.2 and whirlmix, adjust volume to 1 ml, sonicate, one shot only.

5. Buffer exchange protein into MES pH5.2.

6. Dissolve the protein in 5 ml MES pH5.2 to obtain a concentration of 100 ug/ml Add beads to antibody solution and rotate for 24 h at room temp.

After 24 h of coupling:

Wash beads three times in MES ph5.2

Resuspend in 1 ml MES pH6

Proceed to color-coding protocol.

c. Protocol for Color Coding.

Materials:

Alexa 488 maleimide, stock 10 mg/ml in DMSO stored at −70 C

Alexa 647 maleimide stock 10 mg/ml in DMSO stored at −70 C

Buffers: MES pH6.0 with 5 mM EDTA and 1% Tween 20. PBS with 5 mM EDTA and 1% Tween 20.

Tubes: 15 ml Polypropylene tubes, 1.5 ml eppendorf tubes, 1 ml Biorad titer tubes in 96 well rack format.

Procedure:

Beads with thiol groups on (see part 1 of protocol) are suspended in 1-1.5 ml at 10% solids in MES pH6 with EDTA and tween before start.

First part: find the starting concentration for Alexa 647 (variable amounts of —SH groups are consumed when coupling proteins, therefore, we first need to determine how much maleimide dyes we need to add to get a linear decrease in fluorescence with serial dilutions of the dye.

1. Prepare solution of Alexa 647 10 ug/ml by adding 1 ul stock to 1 ml MES pH6.

2. Prepare 10 fold dilutions, i.e. 1 ug, 100 ng, 10 ng and 1 ng, in eppendorf tubes.

3. Add 1 ul of the bead suspension to each tube, incubate 10 min in water bath, mix at least twice during the incubation period.

4. Spin tubes, add MES and run flow cytometry.

5. Choose starting concentration for Alexa 647 that is to be used on particles. The starting concentration should be the highest, where a linear signal can be expected.

Thus, if there is a 10 fold difference in fluorescence of 0.1 and 1 ug, and only a 2 fold between 1 and 10 ug, the linear signal starts at 1 ug. Usually, go a little lower for example 200 ng.

Second part: Determine exactly which concentrations are useful for color coding.

6. Set up 16 15 ml tubes. Label from 1-20. Add 14 ml MES pH6 to the first with a 50 ml pipette and 6 ml to the rest.

7. Adjust the Alexa 647 concentration of tube 1 to the chosen starting concentration.

8. Add 8 ml from tube 1 to tube 2, put on lid and mix well.

9. Repeat this to tube 15, leave tube 16 without any dye. Leave the tubes in wet ice.

10. Add 1 ul bead suspension to each of 16 1.5 ml eppendorf tubes.

11, Add 100 ul of each dye dilution to each tube. Mix well and incubate 15 min at 37 C, mix every 5 min.

12. run Flow cytometry.

13. Choose 11 different concentrations that provide fluorescence signals that can be resolved and one blank.

14. Make sure beads are suspended in at least 1250 ul. Add 100 ul to each of the 12 chosen 15 ml tubes. Mix the tube immediately after adding the beads.

15. Place tubes in 37 C water bath. Mix every 5 min, incubate for 20 min.

16. Place tubes in ice-water, leave for 5 min to cool down. Spin down in refrigerated centrifuge at 4 C.

17. Wash twice in MES pH6. resuspend in MES pH6. 900 ul.

The beads can now be left in the fridge overnight if necessary.

Second dye: Usually Alexa 488 maleimide.

1. Prepare a 10 ug/ml Alexa 488 maleimide solution in MES pH6 by adding 1 ul stock to 1 ml buffer in an eppendorf tube. Make four 10 fold dilutions, i.e. 1 ug, 100 ng, 10 ng and 1 ng.

2. Prepare a mix of the 12 beads that were labeled with Alexa 647 by adding 10 ul of each to an eppendorf tube.

3. Adjust volume to 200 ul.

4. Add 10 ul to each of the 4 dilutions of Ax 488 in eppendorf tubes, mix and place in water bath for 15 min with shaking every 5 min.

5. spin, resuspend in MES pH6 and run FACS, find starting dilution for Ax 488. (see previous section for Ax 647).

6. Set up 15 15 ml tubes. Add 15 ml MES to the first and 5 ml to the rest.

7. Adjust Ax488 to the starting conc. In the first tube.

8. Take out 10 ml and add to tube #2. and continue to tube 15.

9. Leave tubes in ice.

10. Add each of the 12 Ax 647 bead aliquots to titer tubes, place 1, 3, 5, 7, 9, 11 in the first rack and 2, 4, 6, 8, 10, 12 in the second. These are referred to as rows. (i.e. all tubes in each row have the same concentration of Ax 647)

11. Fill up the rows to total 8 columns in each rack.

11. Using an 8 channel pipette, take out 50 ul and add to each of 8 titer tubes in the rack.

12. Leave racks on ice.

13. Using an Eppendorf stepper, add 500 ul of ice cold Ax 488 maleimide dilution to each. Dilution 1, 3, 5, 7, 9, 11, 13, 15 to the first rack, dilutions 2, 4, 6, 8, 10, 12, 14 and blank to the second.

14. Shake tubes individually, put back on ice after shaking.

15. Place racks in a Styrofoam box with 37 C water in the bottom so that the interior of the rack is filled with water, (be careful!)

16. Mix tubes almost continuously for 15 min. Be careful not to spill.

17. after 15 min, centrifuge the racks and wash four times with cold MES. Finally resuspend in PBS tween. (we will determine whether it is useful to add NEM 1 mM during the last washing step with MES to quench free sulfhydryls.)

Example 6

Antibody-coupled particles can be used to detect differences in protein expression between cancer cells and normal cells. This application could have diagnostic utility for example in detecting upregulated oncogenic proteins in cancer cells.

Quantitation of Protein Levels.

Figure 10:
FIG. 10 Quantitation of protein levels.

Cell lysates from an erythroleukemia cell line (K562) and normal leukocytes were labeled with amino-reactive forms of biotin and digoxigenin, respectively. The lysates were mixed and incubated with a mixture of color-coded particles that were coupled with antibodies to cellular proteins. The cartoon to the left in FIG. 10 illustrates binding of labeled molecules from the two cell types to a particle. In this case leukocytes (grey) express two-fold more of the protein than the leukemic cells (dark grey). The flow cytometry plot next to the cartoons data in FIG. 10 obtained with antibodies to leukocyte surface markers (two left diagrams). Particles that mainly capture proteins from leukemia cells are represented as dark grey dots, whereas those that capture from leukocytes are grey. The positions in the array are shown in to the right in FIG. 10. The two diagrams to the right in FIG. 10 show similar analysis for antibodies to signaling proteins. Light grey dots represent particles that bind proteins from both cell types.

Analysis of Molecular Complexes and Fusion Proteins.

Detection of molecular complexes may have diagnostic utility for example by revealing dysregulated cell signaling pathways.

Figure 11:
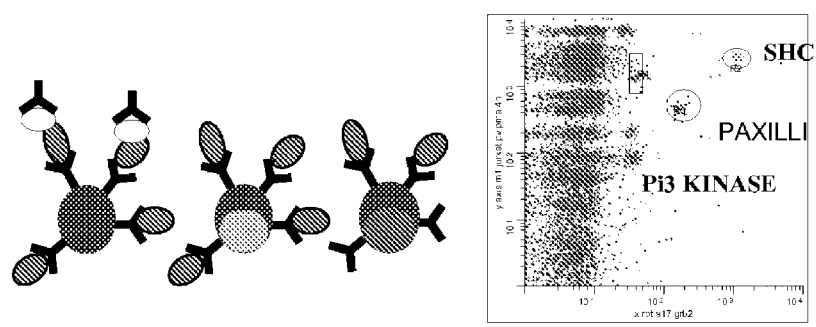
FIG. 11 Analysis of molecular complexes and fusion proteins.

A mixture of particles with antibodies to signaling proteins was first incubated with unlabeled cell proteins and then labeled with antibodies to the adaptor protein grb-2 (cartoon in FIG. 11). Anti-grb2 binds to particles that have captured grb2 either directly with a specific antibody or indirectly via molecules that associate with grb2. Flow cytometric measurement showed that grb-2 was associated with 6 of 96 proteins (populations on the right of the plot in FIG. 11), among these were SHC, PI3 kinase and paxillin, all known to be associated with grb2. The same principle can be used to detect of fusion proteins such as the bcr-abl fusion protein in chronic myeloid leukemia. This shows that protein associations can be analyzed by use of color-coded particles.

Analysis of Protein Phosphorylation.

Figure 12:
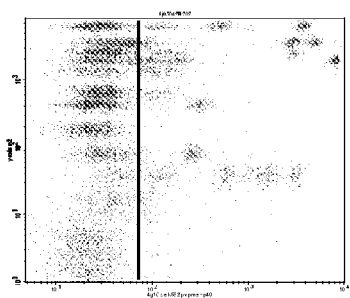
FIG. 12 Analysis of protein phosphorylation.

Protein phosphorylation plays a key role in cell biology and is fundamental for the growth of cancer cells. FIG. 12 shows binding of an anti-phosphotyrosine antibody (x axis) to color-coded particles that were first incubated with a lysate of stimulated K562 erythroleukemia cells. The particle populations that are shown to the right of the vertical line capture proteins that were phosphorylated on tyrosine. The molecules include several known tyrosine kinases (c-abl, lck, ntk, yes, fak).

Figure 13:
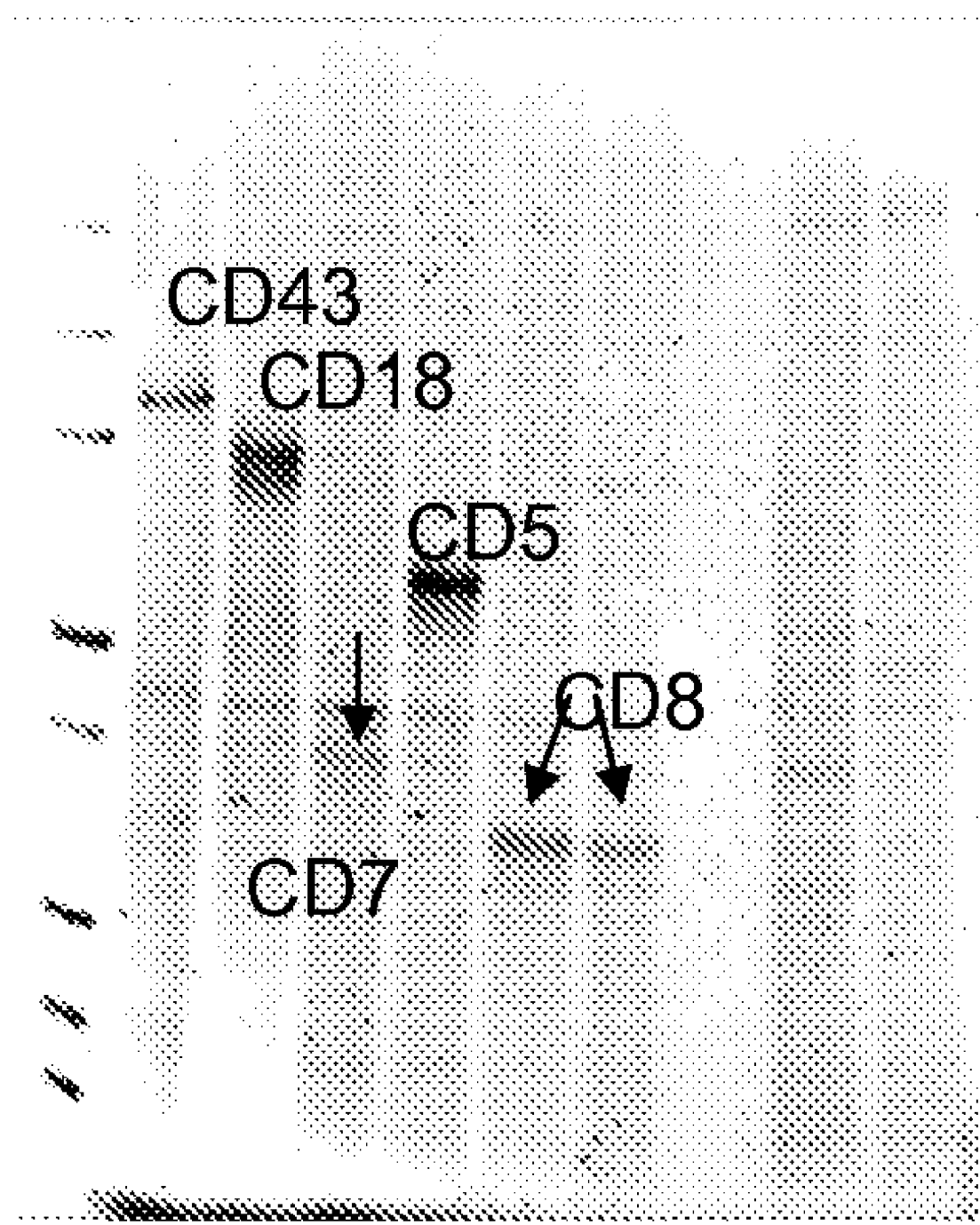
FIG. 13 Verification that signals to particles represent the intended targets of the antibodies on the molecules.

Verification that Signals to Particles Represent the Intended Targets of the Antibodies on the Molecules Color-coded particles with antibodies to leukocyte surface proteins were incubated with fluorescently labeled leukocyte lysates. The particles were boiled and the captured proteins resolved by SDS PAGE. The gel was scanned by a fluorescence scanner. The results show single bands with molecular weight corresponding to the intended targets of the antibodies (FIG. 13). These results show that the technology correctly measures the intended targets of the antibodies.

TABLE 1

| Acronym | PrdNum | Spacer Arm Length | Links | Cleavable By | Water Soluble | Membrane Permeable |
|---|---|---|---|---|---|---|
| Homobifunctional crosslinker chemistry | | | | | | |
| EGS | 21565 | 16.1 Å | Amines To Amines | Hydroxylamine | No | Yes |

TABLE 1-continued

| Name | ID | Length | Reactivity | Cleavable | Membrane permeable | Water soluble |
|---|---|---|---|---|---|---|
| Sulfo-EGS | 21566 | 16.1 Å | Amines To Amines | Hydroxylamine | Yes | No |
| BSOCOES | 21600 | 13 Å | Amines To Amines | Base | No | Yes |
| DSP | 22585 | 12 Å | Amines To Amines | Thiols | No | Yes |
| DTSSP | 21578 | 12 Å | Amines To Amines | Thiols | Yes | No |
| DTBP | 20665 | 11.9 Å | Amines To Amines | Thiols | Yes | Yes |
| DSS | 21555 | 11.4 Å | Amines To Amines | non | No | Yes |
| BS$^3$ | 21580 | 11.4 Å | Amines To Amines | non | Yes | No |
| DMS | 20700 | 11 Å | Amines To Amines | non | Yes | Yes |
| DMP | 21666 | 9.1999998 Å | Amines To Amines | non | Yes | Yes |
| DMA | 20663 | 8.6000004 Å | Amines To Amines | non | Yes | Yes |
| DSG | 20593 | 7.6999998 Å | Amines To Amines | non | No | Yes |
| MSA | 22605 | 7.1999998 Å | Amines To Amines | non | No | nd |
| Sulfo-DST | 20591 | 6.4000001 Å | Amines To Amines | Periodate | Yes | No |
| DST | 20589 | 6.4000001 Å | Amines To Amines | Periodate | No | Yes |
| DFDNB | 21525 | 3 Å | Amines To Amines | non | No | Yes |
| Thiol-maleimide chemistry | | | | | | |
| SMPT | 21558 | 20 Å | Amines To Sulfhydryls | Thiols | No | Yes |
| Sulfo-LC-SMPT | 21568 | 20 Å | Amines To Sulfhydryls | Thiols | Yes | No |
| LC-SMCC | 22362 | 16.1 Å | Amines To Sulfhydryls | non | No | Yes |
| KMUA | 22211 | 15.7 Å | Amines To Sulfhydryls | non | No | nd |
| Sulfo-KMUS | 21111 | 15.7 Å | Amines To Sulfhydryls | non | Yes | No |
| Sulfo-LC-SPDP | 21650 | 15.6 Å | Amines To Sulfhydryls | Thiols | Yes | No |
| LC-SPDP | 21651 | 15.6 Å | Amines To Sulfhydryls | Thiols | No | Yes |
| SMPB | 22416 | 14.5 Å | Amines To Sulfhydryls | non | No | Yes |
| Sulfo-SMPB | 22317 | 14.5 Å | Amines To Sulfhydryls | non | Yes | No |
| SMPH | 22363 | 14.3 Å | Amines To Sulfhydryls | non | No | nd |
| Sulfo-SMCC | 22322 | 11.6 Å | Amines To Sulfhydryls | non | Yes | No |
| SMCC | 22360 | 11.6 Å | Amines To Sulfhydryls | non | No | Yes |
| SIAB | 22329 | 10.6 Å | Amines To Sulfhydryls | non | No | Yes |
| Sulfo-SIAB | 22327 | 10.6 Å | Amines To Sulfhydryls | non | Yes | No |
| Sulfo-GMBS | 22324 | 10.2 Å | Amines To Sulfhydryls | non | Yes | No |
| GMBS | 22309 | 10.2 Å | Amines To Sulfhydryls | non | No | Yes |
| MBS | 22311 | 9.8999996 Å | Amines To Sulfhydryls | non | No | Yes |
| Sulfo-MBS | 22312 | 9.8999996 Å | Amines To Sulfhydryls | non | Yes | No |
| Sulfo-EMCS | 22307 | 9.3999996 Å | Amines To Sulfhydryls | non | Yes | No |
| EMCA | 22306 | 9.3999996 Å | Amines To Sulfhydryls | non | Yes | No |
| EMCS | 22308 | 9.3999996 Å | Amines To Sulfhydryls | non | No | Yes |
| BMPS | 22298 | 6.9000001 Å | Amines To Sulfhydryls | non | No | Nd |
| SPDP | 21857 | 6.8000002 Å | Amines To Sulfhydryls | Thiols | No | Yes |
| SBAP | 22339 | 6.1999998 Å | Amines To Sulfhydryls | non | No | Yes |

TABLE 1-continued

| | | | | | | |
|---|---|---|---|---|---|---|
| BMPA | 22296 | 5.9000001 Å | Amines To Sulfhydryls | non | Yes | No |
| AMAS | 22295 | 4.4000001 Å | Amines To Sulfhydryls | non | No | nd |
| SATP | 26100 | 4.0999999 Å | Amines To Sulfhydryls | non | No | Yes |
| SIA | 22349 | 1.5 Å | Amines To Sulfhydryls | non | No | nd |
| *Carbonyldiimide chemistry* | | | | | | |
| AEDP | 22101 | 9.5 Å | Amines To Carboxyls | Thiols | Yes | No |
| EDC | 22980 | 0 Å | Amines To Carboxyls | non | Yes | No |
| *Photo-affinity chemistry* | | | | | | |
| SASD | 27716 | 18.9 Å | Amines To Nonselective | Thiols | Yes | No |
| SAND | 21549 | 18.5 Å | Amines To Nonselective | Thiols | Yes | No |
| SANPAH | 22600 | 18.200001 Å | Amines To Nonselective | non | No | Yes |
| Sulfo-SANPAH | 22589 | 18.200001 Å | Amines To Nonselective | non | Yes | No |
| Sulfo-NHS-LC-ASA | 27735 | 18 Å | Amines To Nonselective | non | Yes | No |
| SADP | 21533 | 13.9 Å | Amines To Nonselective | Thiols | No | Yes |
| Sulfo-SADP | 21553 | 13.9 Å | Amines To Nonselective | Thiols | Yes | No |
| Sulfo-HSAB | 21563 | 9 Å | Amines To Nonselective | non | Yes | No |
| NHS-ASA | 27714 | 8 Å | Amines To Nonselective | non | No | Yes |
| ANB-NOS | 21451 | 7.6999998 Å | Amines To Nonselective | non | No | No |
| TFCS | 22299 | 7.6999998 Å | Amines To Nonselective | non | Yes | nd |
| Sulfo-SBED | 33033 | Å | Amines To Nonselective | Thiols | Yes | No |
| SPB(NHS-Psoralen) | 23013 | Å | Amines To Nonselective | non | No | Yes |
| *Hydrazine-benzaldehyde chemistry* | | | | | | |
| SANH | | | convertion of amines to aldehydes | | | |
| SHTH | | | convertion of amines to aldehydes | | | |
| SFB | | | convertion of amines to benzaldehydes | | | |
| *Biotin chemistry* | | | | | | |
| *Biotin-derivatives* | | | | | | |
| *Biotin NHS* | | | | | | |
| *Biotin maleimide* | | | | | | |
| *Biotin TFP ester* | | | | | | |

| | Chemical Reactivity | Spacer Arm Length | Cleavable | Water Soluble | Membrane Permeable |
|---|---|---|---|---|---|
| Biotin-BMCC | Sulfhydryl | 32.599998 Å | No | No | Yes |
| Biotin-HPDP | Sulfhydryl | 29.200001 Å | Yes | No | Yes |
| PEO-Maleimide Activated Biotin | Sulfhydryl | 29.1 Å | No | Yes | No |
| Iodoacetyl-LC-Biotin | Sulfhydryl | 27.1 Å | No | No | Yes |
| PEO-Iodoacetyl-Biotin | Sulfhydryl | 24.700001 Å | No | Yes | No |

| Product Name | Chemical Reactivity | Spacer Arm Length | Cleavable | Water Soluble | Membrane Permeable |
|---|---|---|---|---|---|
| Biotin-PEO-LC-Amine | Carboxyl | 22.9 Å | No | Yes | No |
| Biotin-PEO-Amine | Carboxyl | 20.4 Å | No | Yes | No |
| 5-(Biotinamido)-pentylamine | Carboxyl | Å | No | Yes | No |

TABLE 2

Commonly used fluorochromes

| | |
|---|---|
| UV/violet excitable | Alexa 350, Alexa 405, Alexa 430, cascade blue, cascade yellow, |
| 488 excitable | fluorescein, alexa 488, bodipy, R-Phycoerythrin, PerCP, |
| 532 (YAG) excitable | Cy3, Alexa 547, dylight 547, R-phycoerythrin, B-phycoerythrin, Oyster 550, Oyster 556, Atto 520, Atto 532, atto |
| 595 (Krypton) excitable | Texas red, Alexa 610, |
| 633 excitable | Cy5, Cy5.5, Alexa 610, Alexa 633, Alexa 647, Alexa 680, Allophycocyanin, Oyster 645, Oyster 650, Oyster 656 |
| Infrared excitable | Alexa 700, Alexa 750, atto 680, Tandem conjugates of PE and APC (PE = phycoerythrin, APC = allophycocyanine) |
| 488 excitable | PE-Cy5, PE, Cy5.5, PE Alexa 610, PE Texas red, PE-Alexa 680, PE Alexa 633, PerCP Cy5-5 |
| 633 excitable | APC, APC-Cy7, Tandem conjugates of Alexa dyes |
| 488 excitable quantum dots | DyeMer 488-605, DyeMer 488-615, DyeMer 488-630 Lake placid Blue, Adirondack green, Catskill green, Hops Yellow, Birch Yellow, Fort Orange, Adams Apple red, |

The invention claimed is:

1. A set of polymer particles stained with at least two fluorescent dyes, wherein at least 16 subsets of particles can be resolved on the basis of variable emission from the at least two fluorescent dyes, wherein emission from at least one dye of the at least two fluorescent dyes derives from a fluorescent dye covalently attached to a particle surface of at least one particle in the set of polymer particles, wherein all particles in said set of polymer particles can bind a uniform amount of a capture reagent, and wherein the at least two fluorescent dyes are not dyed nanoparticles and are selected from the group consisting of Alexa 488, Alexa 647, Pacific Orange, and Pacific Blue.

2. The set of polymer particles of claim 1, wherein said dyes are attached in defined concentrations.

3. The set of polymer particles according to claim 1, wherein said at least one fluorescent dye that is covalently attached to the particle surface is covalently attached via a bifunctional crosslinker or directly to each particle.

4. The set of polymer particles according to claim 1, wherein all particles in said set of polymer particles contain sufficient binding sites for uniform covalent attachment of capture reagent.

5. The set of polymer particles of claim 4, wherein said binding sites are free SH- or amino-groups.

6. The set of polymer particles according to claim 1, wherein all particles in said set of polymer particles are uniformly labeled with said capture reagent.

7. The set of polymer particles of claim 6, wherein said capture reagent is covalently attached via a bifunctional crosslinker or directly to each particle.

8. The set of polymer particles according to claim 1, wherein the capture reagent optionally has attached fluorescent dyes.

9. The set of polymer particles according to claim 1, wherein said capture reagent is a protein or a nucleic acid.

10. The set of polymer particles according to claim 9, wherein said protein is an antibody-based molecule.

11. The set of polymer particles according to claim 3, wherein the bifunctional crosslinker is based on maleimide-thiol chemistry.

12. The set of polymer particles according to claim 11, wherein the bifunctional crosslinker is SPDP.

13. The set of polymer particles according to claim 1, wherein the fluorescent dyes are UV/violet excitable, 488 nm excitable, 532 nm (YAG) excitable, 595 nm (Krypton) excitable, 633 nm excitable, Infrared excitable, 488 nm excitable, 633 nm excitable Tandem conjugates of PE and APC, Tandem conjugates of reactive dyes, 488 nm excitable and/or quantum dots.

14. The set of polymer particles according to claim 1, wherein the fluorescent dyes are hydrophilic forms of cyanine dyes such as reactive forms of Alexa 488 and 647.

15. The set of polymer particles according to claim 1, wherein the size of each particle is less than 100 μm in diameter.

16. The set of polymer particles according to claim 1, wherein the particles are monodispersed particles.

17. A method for the preparation of the set of polymer particles according to claim 1 comprising, in either sequence:
   a. attaching the at least two fluorescent dyes in defined concentrations to the set of polymer particles, wherein at least one dye is covalently attached to the particle surface; and
   b. optionally attaching different capture reagents of interest to different subsets of polymer particles, wherein said capture reagent may be covalently attached directly to each particle or via a bifunctional crosslinker or biotin-streptavidin and optionally has attached fluorescent dyes.

18. A set of polymer particles prepared according to the method of claim 17.

19. A kit comprising a set of polymer particles according to claim 1.

20. The set of polymer particles according to claim 1, wherein said set of polymer particles is stained with two fluorescent dyes.

* * * * *